United States Patent
Lute, Jr. et al.

(10) Patent No.: US 8,833,169 B2
(45) Date of Patent: Sep. 16, 2014

(54) SYSTEM AND METHOD FOR INSPECTION OF A PART WITH DUAL MULTI-AXIS ROBOTIC DEVICES

(75) Inventors: Thomas William Lute, Jr., Middleburg, PA (US); Brent William Shoffner, Port Matilda, PA (US)

(73) Assignee: General Electric Company, Schenectady, NY (US)

( * ) Notice: Subject to any disclaimer, the term of this patent is extended or adjusted under 35 U.S.C. 154(b) by 356 days.

(21) Appl. No.: 13/316,000

(22) Filed: Dec. 9, 2011

(65) Prior Publication Data

US 2013/0145850 A1 Jun. 13, 2013

(51) Int. Cl.
*G01N 29/04* (2006.01)

(52) U.S. Cl.
USPC .............................................. 73/619; 73/633

(58) Field of Classification Search
USPC ................ 73/619, 598, 599, 600, 633, 865.8; 901/44
See application file for complete search history.

(56) References Cited

U.S. PATENT DOCUMENTS

| | | | | |
|---|---|---|---|---|
| 4,881,177 A | * | 11/1989 | McClean et al. | 700/258 |
| 6,378,387 B1 | * | 4/2002 | Froom | 73/865.8 |
| 6,433,875 B1 | * | 8/2002 | Kovac | 356/498 |
| 7,448,271 B2 | | 11/2008 | Duncan et al. | |
| 7,757,558 B2 | * | 7/2010 | Bossi et al. | 73/609 |
| 7,784,348 B2 | * | 8/2010 | Dubois et al. | 73/621 |
| 8,243,280 B2 | * | 8/2012 | Dubois et al. | 356/502 |
| 2004/0139802 A1 | | 7/2004 | Gripp | |

FOREIGN PATENT DOCUMENTS

| | | |
|---|---|---|
| DE | 10259653 B3 | 4/2004 |
| EP | 1744157 A2 | 1/2007 |
| EP | 2546640 A2 | 1/2013 |
| WO | 8601897 A1 | 3/1986 |
| WO | 0218958 A2 | 3/2002 |
| WO | 02065099 A1 | 8/2002 |
| WO | 2008103209 A1 | 8/2008 |

OTHER PUBLICATIONS

Search Report from corresponding GB Application No. GB1221807.9 dated Feb. 20, 2013.

* cited by examiner

*Primary Examiner* — J M Saint Surin
(74) *Attorney, Agent, or Firm* — Hiscock & Barclay LLP (57) ABSTRACT

This disclosure describes embodiments of a robotic inspection system that uses a pair of multi-axis robotic devices to perform an ultrasonic scan of a part. Each of the multi-axis robotic devices can comprise an end effector that can transmit and/or receive an ultrasonic signal to perform the ultrasonic scan. In one embodiment, the robotic inspection system includes a linear slide assembly that can translate the multi-axis robotic devices independently from one another on either side of the part.

20 Claims, 4 Drawing Sheets

SYSTEM AND METHOD FOR INSPECTION OF A PART WITH DUAL MULTI-AXIS ROBOTIC DEVICES

BACKGROUND OF THE INVENTION

The subject matter disclosed herein relates to non-destructive testing and inspection of a part and, more particularly, to a system that uses multi-axis robotic devices to perform inspection by passing a signal through the part.

Non-destructive inspection ("NDI inspection") involves examining a part without harming the structure or requiring significant disassembly. This type of inspection is advantageous for many applications that require a thorough inspection of the exterior and/or interior of a structure. For example, the aircraft industry uses NDI inspection to inspect aircraft parts for internal and external damage, anomalies, and flaws.

Technicians can perform NDI inspections by manually moving an appropriate sensor over the structure. Examples of NDI inspections can use a variety of sensors including pulse-echo (PE), through-transmission (TT), and shear-wave sensors to obtain data, such as for thickness gauging, detection of laminar anomalies and porosity, and/or crack detection in the part. Manual inspection requires a technician to move the sensor over the structure. In some inspections, the technician must also watch a display to determine the location of the anomalies, if any, in the structure. The quality of the inspection, therefore, depends in large part upon the technician's performance and skill.

Although use of automation (e.g., robots) can remedy many deficiencies of manual inspection, multi-axis robots find little use in NDI inspection to manipulate the sensor relative to the part because of the inability to determine the exact position (relative to the part) of the sensor in real-time. Rather, programs to operate multi-axis robots simply instruct the robot where to go, but not to report the relative position of the sensor. This limitation makes challenging the ability to obtain the position of the sensor with respect to the part, e.g., in three-dimensional space, as the sensor acquires data. Moreover, the limitations of multi-axis robots are more likely to limit application of these robots in combination with through-transmission (TT) sensors, where the ultrasonic signal from the sensor passes through the part from one robot to another.

The discussion above is merely provided for general background information and is not intended to be used as an aid in determining the scope of the claimed subject matter.

BRIEF DESCRIPTION OF THE INVENTION

This disclosure describes exemplary inspection systems, wherein the inspection systems can use multi-axis robots to conduct inspections using, in one example, through-transmission (TT) sensors. The practice of some disclosed embodiments of the inspection system provide a large inspection envelope to accommodate large parts (e.g., aircraft parts) without the cost, complexity, and limitations of inspection systems that typically translate the sensors using gantry-style linear degrees of freedoms.

In one embodiment, the disclosure describes an inspection system for performing a scan of a part. The inspection system comprises a first multi-axis robotic device with a first end effector and a second multi-axis robotic device with a second end effector. The inspection system also comprises a slide assembly comprising a first linear slide and a second linear slide for supporting, respectively, the first multi-axis robotic device and the second multi-axis robotic device thereon. In one example, the first linear slide and the second linear slide are disposed on either side of the part to permit linear movement of the first multi-axis robotic device independent of the second multi-axis robotic device. In another example, during the scan, the first end effector and the second end effector are positioned on opposite sides of the part to exchange a signal between the first robotic device and the second robotic device.

In another embodiment, the disclosure describes an inspection system for implementing a scan of a part. The inspection system comprises a first multi-axis robotic device with a first end effector that can generate an ultrasonic signal and a second multi-axis robotic device with a second end effector that can receive the ultrasonic signal. The inspection system also comprise a controller coupled to each of the first multi-axis robotic device and the second multi-axis robotic device, the controller comprising a processor configured to execute one or more executable instructions. The executable instructions include executable instruction for positioning the first end effector and the second end effector on opposite sides of the part to pass the ultrasonic signal through the part from the first multi-axis robotic device to the second multi-axis robotic device. The executable instructions also include executable instruction for translating the first end effector and the second end effector along a scan path to collect ultrasonic data about the part, the scan path comprising inspection points corresponding to locations on a computer-aided design (CAD) model of the part, the inspection points defining where the ultrasonic data is collected.

In yet another embodiment, the disclosure describes a method for performing an ultrasonic scan of a part with a first end effector and a second end effector disposed on, respectively, a first multi-axis robotic device and a second multi-axis robotic device. The method comprises steps for translating the first end effector and the second end effector along a scan path to collect ultrasonic data about the part, wherein the first end effector transmits an ultrasonic signal and the second end effector receives the ultrasonic signal after the ultrasonic signal passes through the part. The method also comprises steps for generating a display that includes the ultrasonic data and the model of the part, wherein the first multi-axis robotic device can translate independently of the second multi-axis robotic device from a first end to a second end of the part.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

The present disclosure describes embodiments of a robotic inspection system that inspects a part (also "an asset" and/or "an object") using a pair of multi-axis robots. Inspections may use a variety of tools. For purposes of the present disclosure, ultrasonic tools (i.e., tools that can generate an ultrasonic signal) are used to describe the various features and concepts of the robotic inspections systems. However, artisans skilled in the relevant inspection arts will recognize that other types of tools for scanning parts, e.g., to identify defects and anomalies, are likewise applicable to the robotic inspection system discussed herein. In one embodiment, the robotic inspection system can collect ultrasonic data using opposing ultrasonic tools that can pass an ultrasonic signal through the part from one robot to the other. The multi-axis robots support the ultrasonic tool on a moveable arm that, in combination with other moveable structures of the robot, can manipulate the ultrasonic tool through a plurality of degrees of freedom (e.g., X, Y, Z, pitch, yaw, roll).

The robotic inspection systems also include linear slides or rails that translate the robots independently. In one construction, the robots move parallel to one another while maintaining alignment of the ultrasonic tools sufficient to pass the ultrasonic signal through the part. Tolerances for alignment of the opposing ultrasonic tools for this purpose often cannot exceed more than ±1 mm (or about ±0.003 in) for true position alignment between the tips of the ultrasonic tools on the individual robots. The robotic inspection systems below can meet these requirements and, more particularly, overcome limitations inherent in many types of multi-axis robots, wherein tolerances for the actual location of the end effector on these multi-axis robots may exceed the acceptable limits for alignment of the ultrasonic tools.

Embodiments of the robotic inspection system can also correlate the ultrasonic data to a three-dimensional computer-aided design (CAD) model of the part. This feature permits the embodiments to generate and display the data (e.g., ultrasonic data) as part of, and/or as an overlay to, the CAD model. This feature shows defects and faults within the structure of the part, e.g., cracks, disbands, discontinuities, voids, and porosity, all of which could affect the performance of the part.

Figure 1:
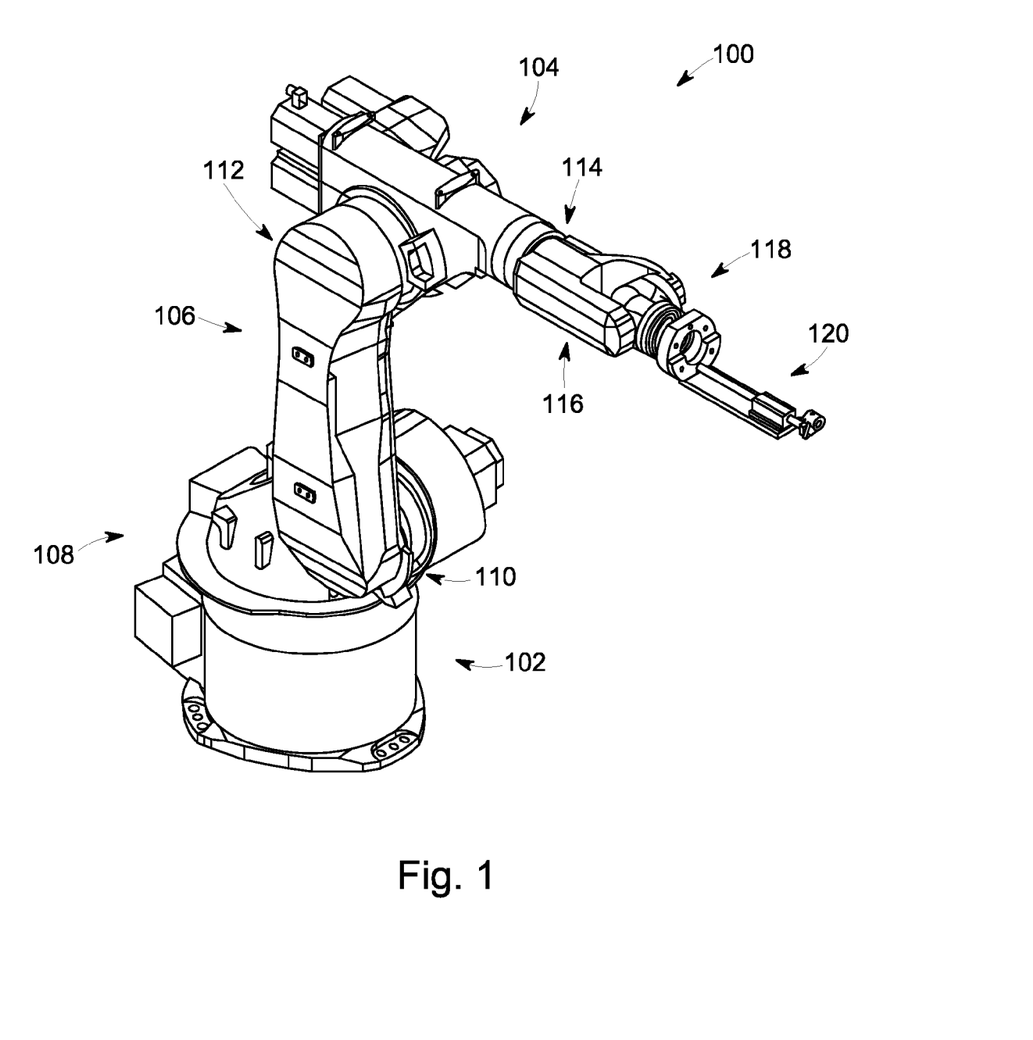
FIG. 1 depicts an exemplary multi-axis robotic device.

FIG. 1 illustrates an exemplary robotic device 100 for use in the inspection systems of the present disclosure. Robots of the type for use as the robotic device 100 are found in industrial settings (e.g., automotive, aircraft, etc.) to automate tasks that would consume substantial human resources. One example of the robotic device 100 is manufactured by Kuka Roboter GmbH (Augsburg, Germany), although any robot with features described herein may be used.

Broadly, and as shown in FIG. 1, the robotic device 100 includes a base 102 a moveable arm 104, and a manipulator 106 that couples the moveable arm 104 to the base 102. The robotic device 100 also includes one or more joints (e.g., a first joint 108, a second joint 110, a third joint 112, a fourth joint 114, a fifth joint 116, and a sixth joint 118). These joints permit the moveable arm 104 and/or manipulator 106 to extend and retract relative to the base 102. In one example, the base 102 can swivel and/or rotate the moveable arm 104 and the manipulator 106. Collectively, these features afford the robotic devices with movement in multiple axes (or "degrees of freedom"). This movement changes the position of an end effector 120 that affixes to the end of the moveable arm 104.

Examples of the end effector 120 can comprise tools and instruments for inspection, including tools that generate ultrasonic signals for performing an ultrasonic scan. In one example, the end effector 120 can mount to the moveable arm 104 in a manner that permits the end effector 120 to be removed and/or re-installed, e.g., to change the type of tool and/or instrument that is on the moveable arm 104. One type of tool may direct ultrasonic signals onto a part and receives ultrasonic signals, e.g., ultrasonic signals that pass through the part and/or that reflect from surfaces of the material of the part. Examples of the end effector 120 can also generate a water jet, which is useful to couple the ultrasonic signal from the tip of the ultrasonic tool to the part surface, and vice versa.

Figure 2:
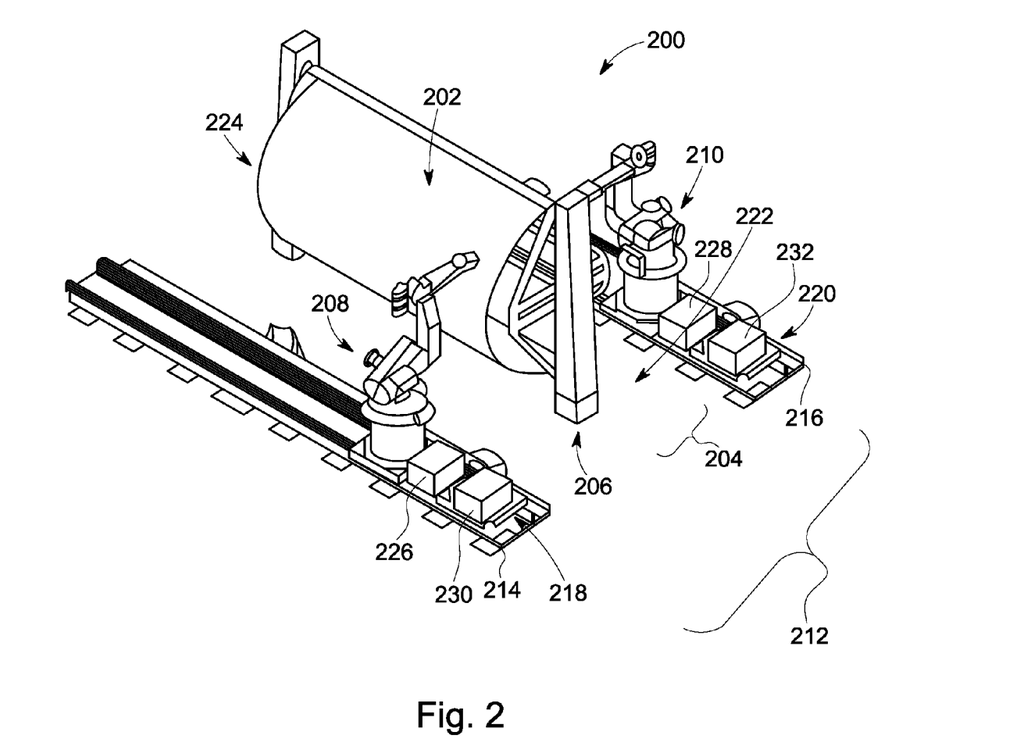
FIG. 2 depicts an exemplary inspection system that includes a pair of the multi-axis robotic devices of FIG. 1.

FIG. 2 depicts an exemplary robotic inspection system 200 that deploys one or more robotic devices (e.g., robotic devices 100 of FIG. 1) to perform ultrasonic inspections on a part 202. The robotic inspection system 200 forms an inspection envelope 204. A part support structure 206 resides in the inspection envelope 204. The part support structure 206 can manipulate the part 202, e.g., by way of rotation and/or vertical translation to change the orientation of the part 202 relative to the robotic devices.

In FIG. 2, the robotic inspection system 200 includes a pair of robotic devices (e.g., a first robotic device 208 and a second robotic device 210) and a linear slide assembly 212 that supports the robotic devices 208, 210. The linear slide assembly 212 includes parallel linear slides (e.g., a first linear slide 214 and a second linear slide 216) on either side of the inspection envelope 204. Tolerances are held very tight over the length of the linear slides 214, 216 and, in one construction, the tolerances are within ±0.05 mm (about ±0.002 in) from end to end. In one example, the linear slides 214, 216 mount to a specially-constructed foundation and/or support structure that maintain these linear tolerances, as well as the planarity and other dimensional aspects necessary for proper orientation of the robotic devices 208, 210 in the robotic inspection system 200.

The linear slides 214, 216 include a carriage (e.g., a first carriage 218 and a second carriage 220) on which the robot devices 208, 210 rest. The carriages 218, 220 can translate along the linear slides 214, 216 to locate the robotic devices 208, 210 at various positions relative to the part 202. Travel of the carriages 218, 220 permits the robot devices 208, 210 to reach both ends (e.g., a first end 222 and a second end 224) of the inspection envelope 204. In one example, the carriages 218, 220 may also support a tool changer (e.g., a first tool changer 226 and a second tool changer 228) and diagnostic instruments (e.g., a first instrument 230 and a second instrument 232) to support operations of the inspection system 200 during scanning. The tool changers 226, 228 can hold one or more tools for use as the end effector (e.g., end effector 120 of FIG. 1). These tools can affix to the moveable arm (e.g., moveable arm 104 of FIG. 1) of the robotic devices 208, 210. Exemplary tools include the ultrasonic tools and devices (e.g., transducers) to perform the ultrasonic scan. Other tools for use with the inspection system 200 may include alignment tools (e.g., a laser, a pointer, etc.) and grippers, although the present disclosure contemplates many different types of tools including tools for use with automated equipment and industrial settings/applications, e.g, found in the aircraft and automotive industries.

For ultrasonic tools like those for use with the inspection system 200, the diagnostic instruments can support various modes of operation. For example, the diagnostic instruments can operate the ultrasonic tools in a single channel mode and in one or more phased array modes, e.g., pulse-echo mode and through-transmission (TT) mode. Artisans skilled in the relevant inspection arts will understand the principle of operation for each of these modes, as well as for the relative construction of the ultrasonic tools to effectuate operation in these various modes.

Figure 3:
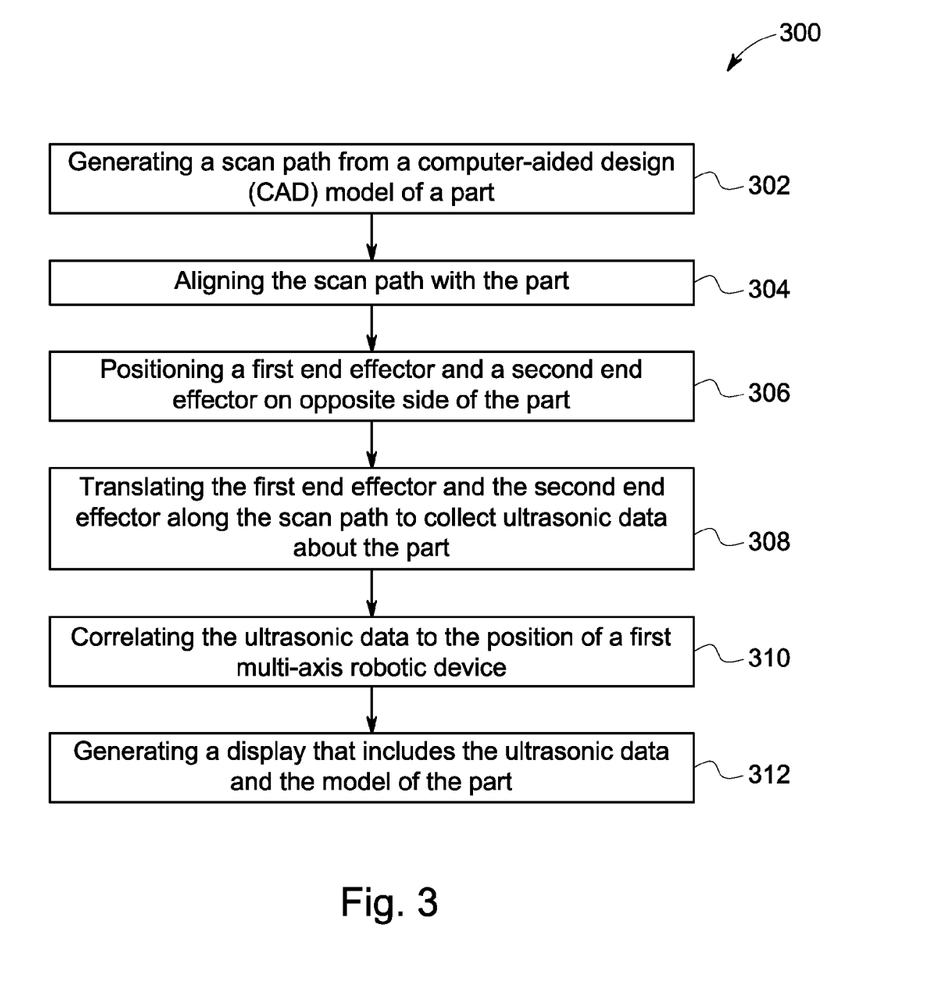
FIG. 3 depicts a flow diagram of an exemplary method of operating an inspection system such as the inspection system of FIG. 2.

FIG. 3 depicts a flow diagram of an exemplary method 300 to operate the robotic devices of the inspection system 200. Execution of these steps can ensure proper alignment of the ultrasonic tools, thereby permitting accurate transfer of the ultrasonic signals through the part 202 from one of the robot devices to the other. One or more of the steps can be coded as executable instructions that, when executed by a processor and/or computing device, cause the robot devices to execute the ultrasonic scan of the part 202.

In FIG. 3, the method 300 includes, at step 302, generating a scan path from a three-dimensional model of a part. The model can be a three-dimensional CAD model from a variety of design software packages, e.g., CATIA. The method 300 also includes, at step 304, aligning the scan path with the part and, at step 306, positioning the first end effector and the second end effector on opposite sides of the part. The method 300 further includes, at step 308, translating the first end effector and the second end effector along the scan path to collect ultrasonic data about the part and, at step 310, correlating the ultrasonic data to the position of a first multi-axis robotic device. The method 300 can also include, at step 312, generating a display that includes the ultrasonic data and the part model.

Figure 4:
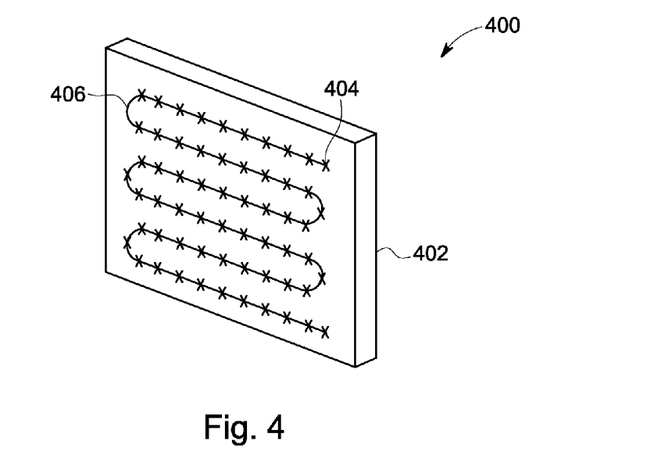
FIG. 4 depicts an example of a scan path that directs operation of the robotic devices in the method of FIG. 3, wherein the scan path can be generated from a computer-aided design (CAD) model of a part.

The step for generating a scan path (e.g., at step 302) defines the position(s) that the robot devices will locate the inspection tool relative to the part during the ultrasonic scan. FIG. 4 illustrates an example of a scan path 400 that results from execution of these steps. The scan path 400 traverses the surface of a CAD model 402, which represents the part that is under inspection. The scan path 400 includes a plurality of inspection points (e.g., inspection point 404) and a scan path line 406 that links the inspection points together. The inspection points define discrete locations on the surface of the part 402 where the inspection system will collect data. Preferences for the scope and the precision of the data will dictate the number and relative spacing of the inspection points. For example, more inspection points that are close together may provide a more accurate reporting of the defects that are found in the part because the inspection system collects more data during the ultrasonic scan.

The step for aligning the scan path with the part (e.g., at step 304) coordinates the scan path with the actual orientation of the part. Execution of this step takes into account the relative position of the components of the inspection system to instruct the robot as to the proper position of the inspection tool in relation to the part. This step may include a step for locating the part in "free space" and, more particularly, may require the robotic device to use an alignment tool or other implement to identify the orientation of the part in the inspection envelope and measure the position of the part relative to the pair of multi-axis robotic devices. The resulting measurements can be used to determine coordinates and/or other indications of the position of the part relative to the multi-axis robotic devices. In one embodiment, the method 300 may include a step for selecting the alignment tool from the tool changer and a step for quantifying the alignment of the part with the alignment tool. For laser-based alignment tools, the method 300 may include a step for directing the laser at one or more locations on the part and, in one implementation, the locations comprise three separate points on the part from which the orientation of the part can be determined.

The steps for positioning and translating the ultrasonic tools (e.g., at steps 306 and 308) move the end effectors (e.g., the first end effector and the second end effector) across the surface of the part. These steps can include one or more steps to energize the various motors and actuators of the robotic devices. The trajectory of the first end effector and the second end effector may depend on the internal software and coding of the robotic devices, e.g., wherein such coding may determine the most efficient combination of movements of the various joints of the robotic devices to position the first end effector and the second end effector in the correct location and to maintain proper alignment for successfully passing of an ultrasonic signal through the part from the first end effector to the second end effector. This movement can cover the entire surface or, in one alternative, cover only a portion of the surface that is known to develop defects or flaws that are detrimental to the part. As discussed above, the scan path can dictate where the first end effector and the second end effector is positioned.

Correlating the ultrasonic data with the position of the first multi-axis robotic device (e.g., at step 310) can use data from at least one of the robotic devices that the robotic devices generate during operation. In one embodiment, and as shown in the schematic diagram below, one or more of the robotic devices may include an encoder or other device that measures movement, position, and/or other parameters of one or more degrees for freedom. Often the information from the encoders is coordinated using one or more matrices that establish the location of the end effector and, ultimately, the ultrasonic tool relative to the coordinate system of the robot. Embodiments of the method 300 may include various steps for mathematical manipulation of the data that defines the position of the robot for use and coordination with the ultrasonic data.

The step for generating a display (e.g., at step 312) can change and/or modify an existing interface that is found on a computer or other computing device. The display can provide a three-dimensional model, on which the ultrasonic data is shown to indicate the data collected during the ultrasonic scan. In one implementation, examination of the display by an end user can indicate where defects may be found. The display may permit the end user to focus on certain areas of the three-dimensional model as well as to provide features for manipulation (e.g., zooming, rotating, etc.) of the resulting model with the ultrasonic data as is generally known in the computing arts.

Figure 5:
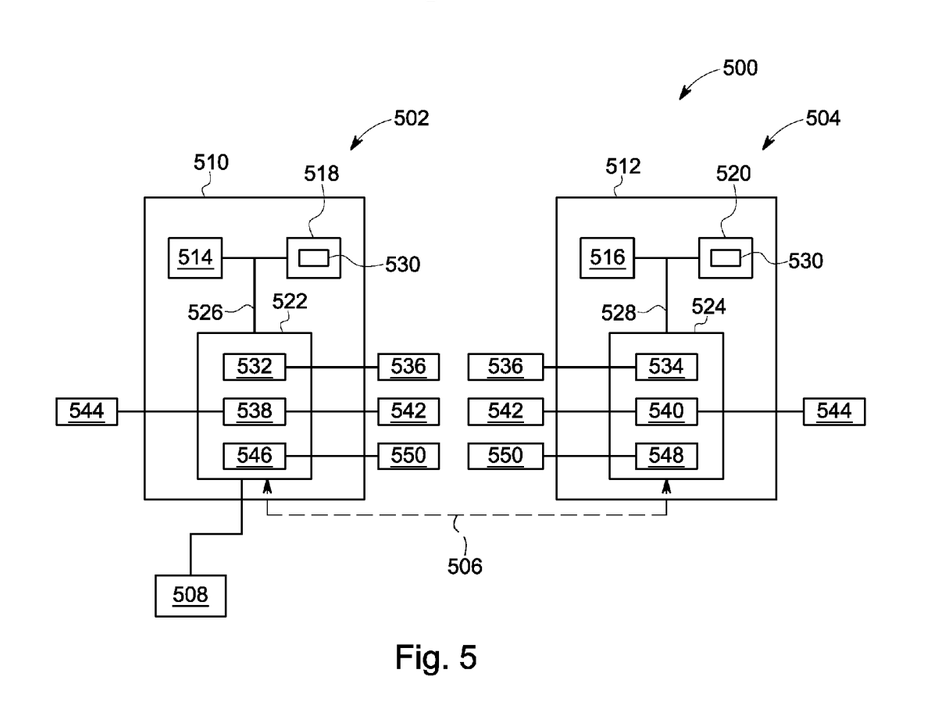
FIG. 5 depicts a wiring schematic of an exemplary inspection system.

FIG. 5 illustrates a high-level wiring schematic of an exemplary inspection system 500. Generally a variety of configurations can implement the concepts of the present disclosure. The example of FIG. 5 provides a schematic diagram of one exemplary structure. In the present example, the inspection system 500 includes a pair of robotic devices (e.g., a master device 502 and a slave device 504) arranged in a master-slave relationship with a data conduit 506 coupled therebetween. In this relationship, the master device 502 dictates the movement, location, and other aspects of operation for the slave device 504. A computing device 508 couples with the master device 502 to communicate executable instructions as well as to exchange data with the robot devices 502, 504. The exchange of data can occur via wired and/or wireless protocols.

The robotic devices 502, 504 include a control unit (e.g., control units 510 and 512), which can include a processor (e.g., processor 514 and 516), a memory (e.g., memory 518 and 520), and drive circuitry (e.g., drive circuitry 522 and 524). These components couple together with a bus (e.g., bus 526 and 528). As also shown in FIG. 5, the memory 518, 520 can store one or more computer programs or executable instructions in the form of, for example, instructions 528 for operating the robotic devices 502, 504 and performing an ultrasonic scan. Examples of the instructions 528 are provided in connection with FIG. 3 discussed above. The steps of the method 300 can be provided as executable instructions, which the components of the robotic devices 502, 504 (including the processor 514, 516 and the drive circuitry 522, 524) can execute to implement and, ultimately, execute the ultrasonic scan disclosed herein.

The drive circuitry 522, 524 can include a motor driver circuit (e.g., motor drive 532 and 534) that operates the various motors 536 for the axes of the robotic devices 502, 504. Motors 536 can include stepper motors and/or deploy encoders to track and determine position of the axes to which the motor 536 is connected. The motor driver circuitry 532, 534 can monitor positions of the encoders, including those encoders associated with the robotic devices 502, 504 and linear drive (not shown). A tool driver circuit (e.g., tool driver circuit 538 and 540) couples with a tool 542 and, in one example, an ultrasonic instrument 544. This combination of components effectuates operation of the ultrasonic scan as described and contemplated herein. The tool driver circuit 538, 540 can also include a tool changer circuit (e.g., tool changer circuit 546 and 548) that couples with a tool changer 550 to permit the robotic devices to change tools as necessary.

Although shown as individual units, variations of construction can combine one or more components of the control units. In one example, the processors are a central processing unit (CPU) such as an ASIC and/or an FPGA. The processors can also include state machine circuitry or other suitable components capable of receiving inputs from the drive circuitry and directly from the other components. The memory can comprise volatile and non-volatile memory and can be used for storage of software (or firmware) instructions and configuration settings. In some embodiments, the processors, the memory, and the driver circuitry can be contained in a single integrated circuit (IC) or other component. As another example, the processors can include internal program memory such as RAM and/or ROM. Similarly, any one or more of functions of these components can be distributed across additional components (e.g., multiple processors or other components).

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An inspection system for performing a scan of a part, comprising:
    a first multi-axis robotic device with a first end effector;
    a second multi-axis robotic device with a second end effector;
    a slide assembly comprising a first linear slide and a second linear slide for supporting, respectively, the first multi-axis robotic device and the second multi-axis robotic device thereon,
    wherein the first linear slide and the second linear slide are disposed on either side of the part and are configured to permit linear movement of the first multi-axis robotic device independent of, and relative to, the second multi-axis robotic device, and
    wherein, during the scan, the first end effector and the second end effector are positioned on opposite sides of the part to exchange a signal between the first robotic device and the second robotic device.

2. The inspection system of claim 1, further comprising a first tool changer and a second tool changer, wherein the first multi-axis robotic device is configured to access the first tool changer and the second multi-axis robotic device is configured to access the second tool changer to change the first end effector and the second end effector from a tool that generates the signal to an alignment tool to measure the position of the part.

3. The inspection system of claim 2, wherein the alignment tool comprises a laser.

4. The inspection system of claim 1, further comprising a first diagnostic tool coupled with the first end effector, wherein the first diagnostic tool configures the first end effector to generate an ultrasonic signal.

5. The inspection system of claim 1, wherein the first end effector and the second end effector are configured to generate a fluid stream to couple the signal from the first end effector to the part and from the part to the second end effector.

6. The inspection system of claim 5, wherein the fluid is water.

7. The inspection system of claim 1, wherein the first multi-axis robotic device and the second multi-axis robotic device have six degrees of freedoms.

8. The inspection system of claim 1, wherein the first multi-axis robotic device is configured to act as a master device and the second multi-axis robotic device is configured to act as a slave device, and wherein the slave device is configured to move in response to movement of the master device.

9. An inspection system for implementing a scan of a part, comprising:
    a first multi-axis robotic device with a first end effector that is configured to generate an ultrasonic signal;
    a second multi-axis robotic device with a second end effector that is configured to receive the ultrasonic signal; and
    a controller coupled to each of the first multi-axis robotic device and the second multi-axis robotic device, the controller comprising a processor configured to execute one or more executable instructions including executable instruction for:
    positioning the first end effector and the second end effector on opposite sides of the part to pass the ultrasonic signal through the part from the first multi-axis robotic device to the second multi-axis robotic device; and
    translating the first end effector and the second end effector along a scan path to collect ultrasonic data about the part, the scan path comprising inspection points corresponding to locations on a computer-aided design (CAD) model of the part, the inspection points defining where the ultrasonic data is collected.

10. The inspection system of claim 9, further comprising a first linear slide and a second linear slide supporting, respectively, the first multi-axis robotic device and the second multi-axis robotic device on opposite sides of the part, wherein the first linear slide is configured to translate independently of and parallel to the second linear slide.

11. The inspection system of claim 9, further comprising a first diagnostic tool coupled with the first end effector, wherein the first diagnostic tool configures the first end effector to generate an ultrasonic signal.

12. The inspection system of claim 9, further comprising executable instructions for measuring the position of the part relative to the first multi-axis robotic device, wherein the scan path is aligned with the position of the part prior to implementation of the scan of the part.

13. The inspection system of claim 12, further comprising executable instructions for retrieving an alignment tool with a laser with the first multi-axis robotic device to measure the position of the part relative to the first multi-axis robotic device.

14. The inspection system of claim 9, wherein the first multi-axis robotic device is configured to act as a master device and the second multi-axis robotic device is configured to act as a slave device, and wherein the slave device is configured to move in response to movement of the master device.

15. A method for performing an ultrasonic scan of a part with a first end effector and a second end effector disposed on, respectively, a first multi-axis robotic device and a second multi-axis robotic device, said method comprising steps for:
    translating the first multi-axis robotic device and the second multi-axis robotic device to position the first end effector and the second end effector along a scan path to collect ultrasonic data about the part, wherein the first end effector is configured to transmit an ultrasonic signal and the second end effector receives the ultrasonic signal after the ultrasonic signal passes through the part; and generating a display that includes the ultrasonic data and the model of the part, wherein the first multi-axis robotic device and the second multi-axis robotic device are configured for linear movement, and wherein the first multi-axis robotic device is configured to translate independently of, and relative to, the second multi-axis robotic device from a first end to a second end of the part.

16. The method of claim 15, further comprising a step for generating the scan path from a computer-aided design (CAD) model of the part.

17. The method of claim 15, further comprising a step for measuring the position of the part relative to the first multi-axis robotic device and a step for aligning the scan path with the position prior to implementation of the ultrasonic scan.

18. The method of claim 15, further comprising a step for correlating the ultrasonic data to the position of the first multi-axis robotic device.

19. The method of claim 15, wherein the first multi-axis robotic device and the second multi-axis robotic devices have six degrees of freedom.

20. The method of claim 15, wherein the first end effector and the second end effector generate a stream of water to couple the ultrasonic signal from the first end effector to the part and from the part to the second end effector.

* * * * *